US 011872387B2

(12) United States Patent
Stallard et al.

(10) Patent No.: US 11,872,387 B2
(45) Date of Patent: Jan. 16, 2024

(54) TRIAL NEUROSTIMULATION SYSTEM WITH A LEAD ADAPTER

(71) Applicant: Saluda Medical Pty Limited, Macquarie Park (AU)

(72) Inventors: Phil Stallard, Macquarie Park (AU); John Louis Parker, Macquarie Park (AU)

(73) Assignee: Saluda Medical Pty Limited, Macquarie Park (AU)

( * ) Notice: Subject to any disclaimer, the term of this patent is extended or adjusted under 35 U.S.C. 154(b) by 90 days.

(21) Appl. No.: 17/387,831

(22) Filed: Jul. 28, 2021

(65) Prior Publication Data

US 2022/0032039 A1    Feb. 3, 2022

(30) Foreign Application Priority Data

Jul. 28, 2020  (AU) .................................. 2020902650

(51) Int. Cl.
*A61N 1/04*       (2006.01)
(52) U.S. Cl.
CPC ..................................... *A61N 1/04* (2013.01)
(58) Field of Classification Search
CPC ..... A61N 1/04; A61N 1/3625; A61N 1/37235
See application file for complete search history.

(56) References Cited

U.S. PATENT DOCUMENTS

| 5,906,634 | A | 5/1999 | Flynn et al. |
| 6,741,892 | B1 | 5/2004 | Meadows et al. |
| 7,020,525 | B1 | 3/2006 | Davis et al. |
| 7,337,003 | B2 | 2/2008 | Malinowski |
| 8,639,340 | B2 * | 1/2014 | Sommer .............. A61N 1/3752 607/37 |
| 2004/0186542 | A1 | 9/2004 | van Venrooij et al. |
| 2008/0312707 | A1 | 12/2008 | He et al. |
| 2011/0065301 | A1 | 3/2011 | Boyd et al. |
| 2019/0105501 | A1 | 4/2019 | Howard et al. |
| 2021/0008376 | A1 * | 1/2021 | McBride ................ A61N 1/378 |

OTHER PUBLICATIONS

AU; Australian International-Type Search Report in the Australian Provisional Patent Application No. 2020902650 dated Jan. 13, 2021.

* cited by examiner

*Primary Examiner* — Alyssa M Alter
(74) *Attorney, Agent, or Firm* — KPPB LLP (57) ABSTRACT

A system adapted for neurostimulation of a patient, using a trial stimulator unit for generating stimulation pulses to targeted tissue in a patient through at least one neurostimulation lead. The trial stimulator unit has at least one receiving connection port adapted to receive at least one lead adapter. The lead adapter has a receiving portion, a sliding portion and a connection port. The receiving portion receives a proximal end of a stimulation lead. The sliding portion couples to the receiving portion. The connection port is adapted to connect to at least one receiving connection port. A case for enclosing the trial stimulator unit and the at least one lead adapter is provided.

24 Claims, 5 Drawing Sheets

TRIAL NEUROSTIMULATION SYSTEM WITH A LEAD ADAPTER

TECHNICAL FIELD

The present invention relates to electronic tissue stimulators and more particularly to electronic tissue stimulators adapted for use in stimulation trial situations.

BACKGROUND OF THE INVENTION

Neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord or dorsal root ganglion (DRG). Such a system typically comprises an implanted electrical pulse generator and a power source such as a battery that may be rechargeable by transcutaneous inductive transfer. An electrode array is connected to the pulse generator and is positioned in the dorsal epidural space above the dorsal column. An electrical pulse applied to the dorsal column by an electrode causes the depolarization of neurons and generation of propagating action potentials. The fibres being stimulated in this way inhibit the transmission of pain from that segment in the spinal cord to the brain.

Generally, neurostimulation therapy includes implanting a pulse generator in the body of a patient and stimulating a target neuron or muscle using the stimulation leads that are electrically coupled to the pulse generator. This is an invasive process which is done with the help of surgery. During the surgery, one or more leads with electrodes thereon suitable for providing neurostimulation may be implanted within the targeted anatomy of the patient. For example, the leads may be implanted in a dorsal column of the patient if the patient is undergoing therapy for chronic pain.

During the implantation of the leads, the physician may connect the leads to a pulse generator and stimulate the tissue of the patient to check if the position of the leads and stimulation intensity are producing the desired results to the patient. The implanted pulse generator (IPG) may be connected to external devices such as a clinical programmer and remote control for modifying the characteristics of the neuromodulation therapy. For instance, the characteristics of the neuromodulation therapy may include a stimulation frequency, stimulation intensity, electrode location and the like.

Alternatively, the patients may not be comfortable with a permanent implant and may wish to experience the neurostimulation on a trial basis before receiving a permanently implanted pulse generator. In such cases, there exists a trial implant procedure where the pulse generator is not implanted in the patient. However, the leads still need to be implanted in the patient. The proximal end of the leads may be implanted using laparoscopic methods with local anaesthesia. Thereafter, the proximal end of the leads may be coupled with an external pulse generator, and stimulation pulses may be delivered to the target anatomy. This way the trial may be carried out for a period of 7 to 30 days or more.

It is desired to have a trial stimulator system which provides reliable connections between and leads and the trial stimulator and is easy to operate.

Any discussion of documents, acts, materials, devices, articles or the like which have been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present disclosure provides a system adapted for neurostimulation of a patient, the system comprising: a trial stimulator unit for generating stimulation pulses to a targeted tissue in a patient through at least one neurostimulation lead, wherein the trial stimulator unit comprises at least one receiving connection port, wherein the receiving connection port is adapted to receive at least one lead adapter; at least one lead adapter comprising a receiving portion, a sliding portion and a connection port, wherein the receiving portion is adapted to receive a proximal end of a stimulation lead and the sliding portion is configured to couple to the receiving portion, wherein the connection port is adapted to connect with at least one receiving connection port; and a case adapted to enclose the trial stimulator unit and the at least one lead adapter. In some examples, the case comprises a first portion and a second portion.

In some embodiments of the invention, the receiving portion of the at least one lead adapter may comprise a receiving channel to receive a proximal end of a neurostimulation lead.

In some embodiments of the invention, the sliding portion comprises a retention strip configured to exert pressure on the proximal end of the neurostimulation lead to assist retention of the neurostimulation lead in the receiving channel. The retention strip is, for example, a raised rib which is above the level of the sliding portion. In an exemplary embodiment, the retention strip has an elongated rectangular pattern, In some embodiments of the invention, the receiving portion comprises a stylet slot to receive a stylet, wherein the stylet is used to guide the lead to a desired location in the anatomy of a patient.

In some embodiments of the invention, the receiving portion comprises at least one locking portion and the sliding portion comprises at least one locking groove, wherein the locking groove is adapted to engage with the locking portion to lock the sliding portion to the receiving portion.

In some embodiments of the invention, trial stimulator unit may have a substantially cuboid profile. In some alternate embodiments, the trial stimulator unit may have a substantially cylindrical profile.

In some embodiments of the invention, the trial stimulator unit includes a battery enclosed by at least one of the first surface and the second surface.

In some embodiments of the invention, the sliding portion of the plurality of lead adapters may be coupled to the receiving portion at a terminal end by a hinged means. Alternatively, the lead adapter may have a single component without the sliding portion.

Since the lead adapter can be detached from the trial stimulator unit, a surgeon can adjust the lead position in the patient by using the stylet which emerges out of the lead adapter. This is an advantage of the lead adapter disclosed herein. Further, the lead adapter may include a retention strip whose thickness can be adjusted for exerting a required pressure of the lead contacts for improved electrical coupling between the lead contacts and the electrical contacts within the lead adapter. In an embodiment, the sliding portion of the plurality of lead adapters includes one or more protrusions for better handling. Alternatively, the surface of the sliding portion may be altered for better grip and handling.

In some additional embodiments of the invention, the trial stimulator unit comprises a battery coupled to at least one of a first surface and a second surface of the trial stimulator unit.

In some embodiments of the invention, the sliding portion of the lead adapter is coupled to the receiving portion by a hinged means. In such an embodiment, the sliding portion may be configured to cover at least a portion of the receiving portion. In some embodiments, the sliding portion is hinged to the receiving portion at a suitable point.

In some embodiments of the invention, the sliding portion comprises one or more protrusions for better grip. For instance, the protrusions may be composed to a different material to impart better handling capabilities.

In some embodiments of the invention, the case comprises a first portion and a second portion. In some other embodiments, the case may be a silicone based wrap which accommodates the trial stimulation unit and the lead adapters. Further, the silicone based wrap may render the trial stimulation system waterproof.

In some alternate embodiments of the invention, the first portion and the second portion of the case comprises a waterproof seal. The waterproof seal may be fabricated from a material such as epoxy, silicone or rubber which prevents or resists fluid from entering the case, when the case is in a closed state.

In some further embodiments of the invention, the first portion and the second portion of the case form at least one aperture, configured to accommodate the neurostimulation lead, when the case is in a closed state. Alternatively, the either the first portion or the second portion of the case may include an aperture to accommodate the neurostimulation lead.

In some alternate embodiments of the invention, the case further includes one or more flaps for aiding opening and closing of the case. Alternatively, the case may include a locking mechanism for opening and closing the case.

In some embodiments of the invention, the plurality of lead adapters and the case are fabricated using materials from a group comprising plastic, epoxy, polyurethane materials. Alternatively, surgical grade metals such as stainless steel and platinum may be used wherever appropriate.

In some embodiments of the invention, the battery of the trial stimulator unit is at least one of a Lithium-Ion battery, a Lithium Polymer battery and an alkaline battery. In some cases, the battery may be charged using wireless charging methods or employing solar power.

In some other embodiments of the invention, at least one of the first portion and the second portion of the case may include a waterproof seal. The waterproof seal may be embedded into the first portion and the second portion of the case.

In some embodiments of the invention, the case further includes a plurality of flaps for aiding opening and closing thereof. The flaps may be in the form of semicircular protrusions. In some alternate embodiments, the first portion and the second portion may be opened and closed using a locking mechanism. In some instances, the outer surface of the cover may include at least one of a display unit and a solar module. The display unit may be configured to display one or more parameters of the trial stimulator unit such as, but not limited to, a battery status, a stimulation program and a mode of operation. In an exemplary embodiment, the battery associated with the trial stimulator unit may be recharged using the solar module disposed on the outer surface of the cover.

In some further embodiment of the invention, the trial stimulator unit, the plurality of lead adapters and the case are fabricated in plastic. In some cases, the trial stimulator unit, the plurality of lead adapters and the case are 3D printed using various materials including, but not limited to, epoxy, silicone and PVC.

In some additional embodiments of the invention, the battery is a Lithium-Ion battery. In some other embodiments, the battery may be at least one of a Lithium-Polymer battery and a rechargeable alkaline battery.

In a second aspect of the invention, there is provided lead adapter for use with a trial neurostimulation system, the lead adapter comprising: a receiving portion including a receiving channel to receive a proximal end of a neurostimulation lead; and a sliding portion, wherein the sliding portion is configured to slidingly couple with the receiving portion.

In some embodiments of the invention, the receiving portion comprises at least one locking portion and the sliding portion comprises at least one locking groove, wherein the locking groove is adapted to couple with the locking portion enabling the sliding portion to slidingly couple with the receiving portion.

In some other embodiments of the invention, the sliding portion includes lateral walls, with inwardly extending retention lips that are slidingly receivable over at least part of the receiving portion.

In further embodiments of the invention, the sliding portion comprises a retention strip configured to exert pressure on the proximal end of the neurostimulation lead to assist retention of the neurostimulation lead in the receiving channel.

In further embodiments of the invention, the retention strip of the lead adapter is removable.

In some additional embodiments of the invention, a thickness of the retention strip is between a range of 0.5 mm to 1 mm.

In some embodiments of the invention, the sliding portion comprises a plurality of protrusions to provide grip to the sliding portion. The protrusions may be composed of a material such as a plastic, rubber, epoxy and silicone, which may impart additional grip.

In some embodiments of the invention, the receiving portion comprises at least one locking portion and the sliding portion comprises at least one locking groove, wherein the locking groove is adapted to couple with the locking portion enabling the sliding portion to slidingly couple with the receiving portion.

In some embodiments of the lead adapter, the sliding portion comprises a retention strip configured to exert pressure on the proximal end of the neurostimulation lead to assist retention of the neurostimulation lead in the receiving channel.

In some embodiments of the lead adapter, the retention strip is removable. In some examples, the thickness of the retention strip is between a range of 0.5 mm to 1 mm. In some examples of the lead adapter, the sliding portion comprises a plurality of protrusions to provide grip to the sliding portion.

According to a third aspect of the invention provides, a case for enclosing a trial stimulation unit and at least one lead adapter, the case comprising:
- a first portion; and
- a second portion,
  - wherein the first portion is coupled with the second portion via a hinge; and
  - wherein the first portion and the second portion is adapted to releasably contain at least a portion of the trial stimulator unit and at least one lead adapter.

In some embodiments of the invention, the case is configured to releasably contain the trial stimulator unit, whereby the trial stimulator unit may be securely held by the case when the case is closed, and whereby the trial stimulator unit may be manually removed from the case when the case is open. For example the first portion and/or second portion of the case may comprise one or more lugs positioned to hold the trial stimulator unit in a friction fit, while permitting a user to retrieve the trial stimulator by hand by overcoming the friction fit.

In some embodiments of the invention, an aperture is formed when the case is in a closed state.

In some such embodiments of the invention, the at least one aperture is adapted to accommodate at least one neurostimulation lead.

In some embodiments of the invention, at least one aperture is formed when the case is in a closed state. In further embodiments, at least one aperture is adapted to accommodate at least one neurostimulation lead.

In some embodiments of the invention, at least one of the first portion and the second portion comprises a waterproof or a water-resistant seal which renders the case waterproof in a closed state.

BRIEF DESCRIPTION OF THE DRAWINGS

An example of the invention will now be described with reference to the accompanying drawings, in which.

DESCRIPTION OF THE PREFERRED EMBODIMENTS

Figure 1:
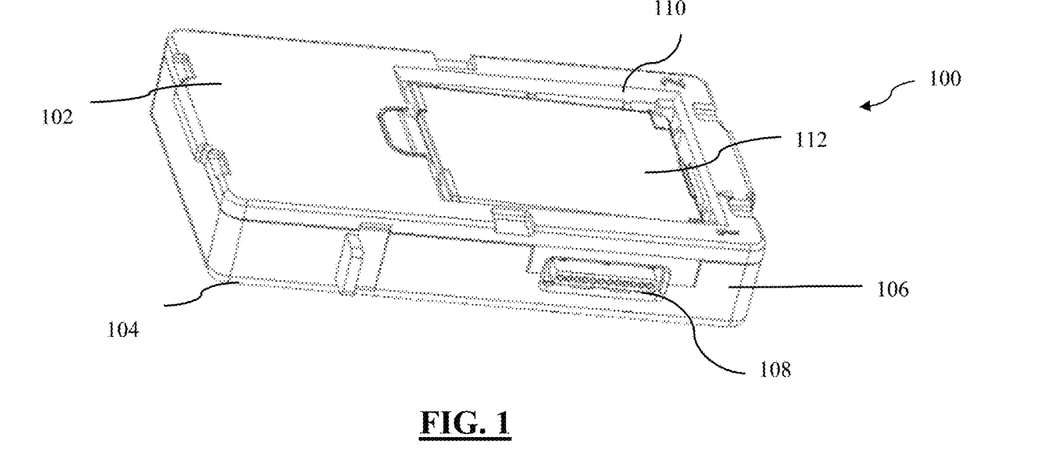
FIG. 1 illustrates a trial stimulator unit in accordance with an embodiment.

The trial stimulator system comprises a trial stimulator unit 100, a plurality of lead adapters 200 and a case 300. FIG. 1 illustrates a trial stimulator unit 100 which is a part of the trial stimulator system disclosed in the present invention. Trial stimulator unit 100 includes a first surface 102, a second surface 104, an adjacent surface 106, a plurality of receiving connection ports 108, a battery slot 110 and a battery 112. The trial stimulator unit 100 may have a substantially cuboid profile. The first surface and the second surface are adapted to be enclosed by a case 300 (explained in conjunction with FIGS. 3A and 3B). The trial stimulator 100 houses a pulse generation unit (not shown) configured to deliver therapeutic pulses to target anatomy of the patient via the implanted leads. Adjacent surface 106 includes a receiving connection port 108 which receives a lead adapter 200 to establish electrical connection between the lead adapter 200 and the pulse generation unit. The trial stimulator 100 encloses a Printed Circuit Board (PCB) which includes a control unit (not shown) for controlling the stimulation pulses delivered through the leads, such as lead 208. The PCB may further include an antenna to communicate with external devices such as a clinical programmer and remote control.

In a preferred embodiment, the trial stimulator unit 100 includes a battery slot 110 on the first surface 102. The battery slot 110 houses the battery 112. The profile of the battery slot 110 may be in accordance with the shape of the battery 112. For example, if a battery 1112 has a cuboid profile the battery slot, 110 may have a profile to accommodate the profile of the battery 112. The battery 112 may include several variants including, but not limited to, a Lithium-Ion battery, an alkaline battery and a Lithium-Polymer battery. In some embodiments, the battery slot may be located on, at least one of, the second surface 104 and inside the trial stimulator unit 100. In further embodiments, the receiving connection port 108 may be located on any region of the adjacent surface 106. In a preferred embodiment, the receiving connection port 108 may include a 1/12 channel receptacle on either side of the trial stimulator unit 100. The number of channels in the port is dependent on the number of electrodes in the leads. As shown in FIG. 1, the trial stimulator 100 may have several grooves and protrusions 209 for providing stability when enclosed with the case 300.

Figure 2A:
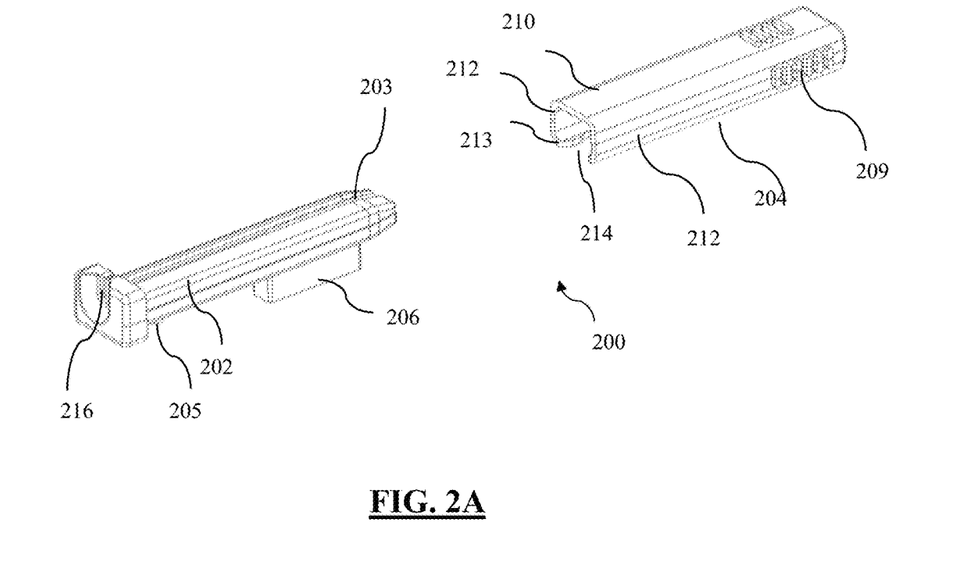
FIG. 2A illustrates a perspective view of a lead adapter, in accordance with an embodiment.
Figure 2B:
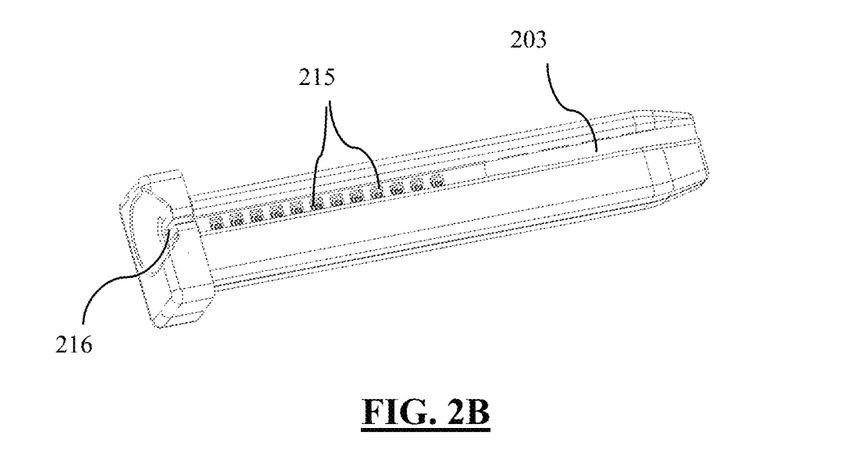
FIG. 2B illustrates a top view of the receiving portion of the lead adapter, in accordance with an embodiment.
Figure 2C:
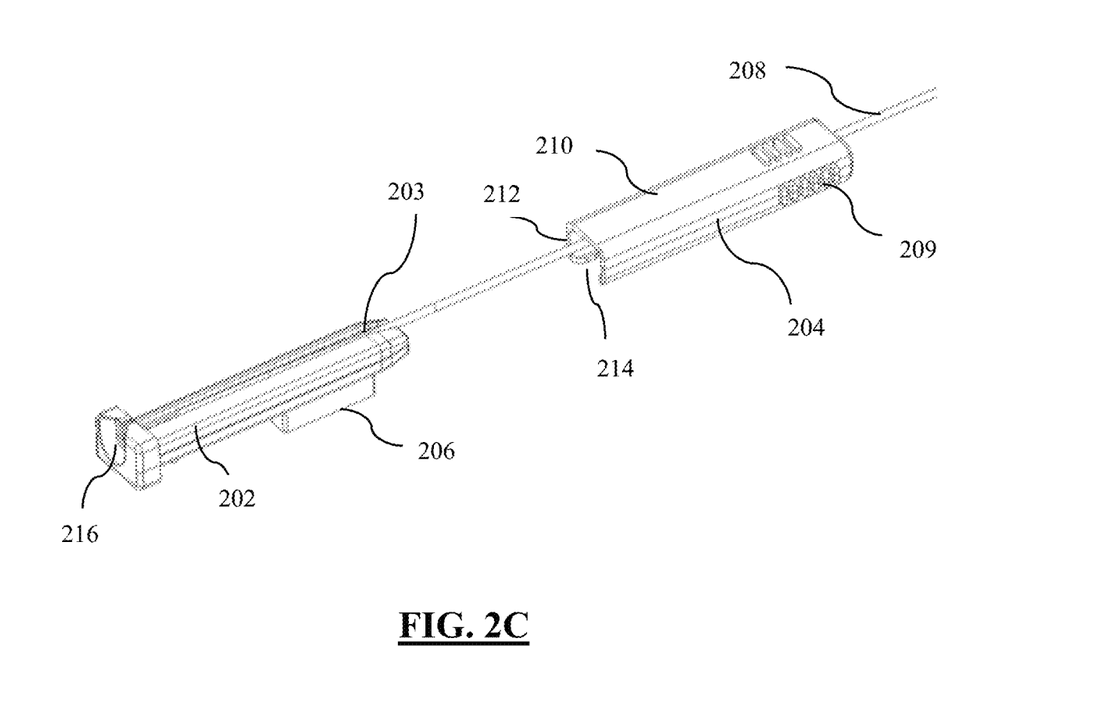
FIG. 2C illustrates a perspective view of a lead adapter with a lead inserted, in accordance with an embodiment.

FIG. 2A illustrates a lead adapter 200 for use in the trial neurostimulation system. The lead adapter 200 includes a receiving portion 202, a sliding portion 204 and a connection port 206. The receiving portion 202 is adapted to receive a proximal end of a stimulation lead 208. As mentioned before, the distal end of the stimulation lead 208 is implanted in target anatomy of the patient whereas the proximal end is inserted into the receiving portion 202 of the lead adapter 200. The receiving portion 202 includes a plurality of electrical contacts 215 which establish electrical connection between the electrode contacts on the lead 208 to the connection port 206. FIG. 2B illustrates a top view of the receiving portion in accordance with some embodiments. Further, the sliding portion 202 is configured to slidingly couple to the receiving portion 204. The sliding portion 202 is hollow and cuboid in shape. The sliding portion 202 may be fabricated to correspond with the shape of the receiving portion 202. In an exemplary embodiment, the receiving portion 202 may be having a cylindrical profile. In such a case, the sliding portion 204 would be fabricated to have a corresponding cylindrical profile in order to couple to the receiving portion 202. In a preferred embodiment, the receiving portion 202 may have a cuboid profile, and the sliding portion 204 may also have a cuboid profile to match the receiving portion 202. The sliding portion 204 is hollow and has an upper wall 210 and lateral walls 212. The sliding portion 204 has void 214 which aids in avoiding interference with the connection port 206. In some embodiments, the lateral walls 212 have one or more inwardly extending retention lips 213 that are slidingly received over at least part of the receiving portion 202. In some examples, the retention lips 213 may engage with a groove of the receiving portion 202. Thus the inwardly extending retention lips 213 assists in retaining the sliding portion 204 to the receiving portion. Furthermore, as illustrated in FIG. 2C, the length of the retention lips 213 may extend substantially in the same axis as the receiving channel 203 and proximal end of the lead 208 (as well as the same movement axis of the sliding portion 202 and the receiving portion 202). This allows the sliding portion 202 to slide over the lead 208 during assembly without interference. The sliding portion 204 protects the proximal portion of the lead from being exposed and provides stability to the lead adapter 200.

In some embodiments, the receiving portion 202 and the sliding portion 204 may be coupled to each other using a hinged means. In yet another embodiment, the lead adapter 200 includes a receiving channel 203 configured to receive a lead. In further embodiments, the receiving portion 202 may have a plurality of receiving channel 203, and connection ports to enable receiving a plurality of leads. The trial stimulator 100 may be modified in accordance with the changes in the receiving portion 202. A person skilled in the art may appreciate that there may be many such modifications to improve the functionality of the system.

FIG. 2C illustrates the lead adapter 200 with a proximal portion of lead 208 inserted in accordance with an embodiment. The lead 208 may have several electrodes ranging from 6 to 24. The lead is received in a receiving channel 203 of the receiving portion 202. The receiving channel 203, as shown in FIG. 2B, may include electrical contacts 215, aligned with the electrodes of the lead 208, establishing an electrical connection between the electrodes of the lead 208 and the connection port 206. The connection port 206 includes electrical contacts corresponding to the receiving connection ports 108. Further, as shown in FIG. 2C the sliding portion 204 may slidingly lock onto at least a portion of the receiving portion 202.

In a preferred embodiment, the receiving portion 202 includes a locking portion 205 and the sliding portion 204 includes grooves 207. When the sliding portion 204 slides onto the receiving portion 202, the locking grooves 207 engage with the locking portion 205 thereby holding the sliding portion 204 firmly on the receiving portion 202. The sliding portion 204 covers the slot 203 along with the lead inserted into the slot 203. The sliding portion 204 may include one or more protrusions 209 for better grip. In some embodiments, the protrusions 209 may be composed of a different material than that of the sliding portion 204. For example, the protrusions 209 may be made up of a material such as, but not limited to, rubber, epoxy and material of a higher durometer.

Figure 2D:
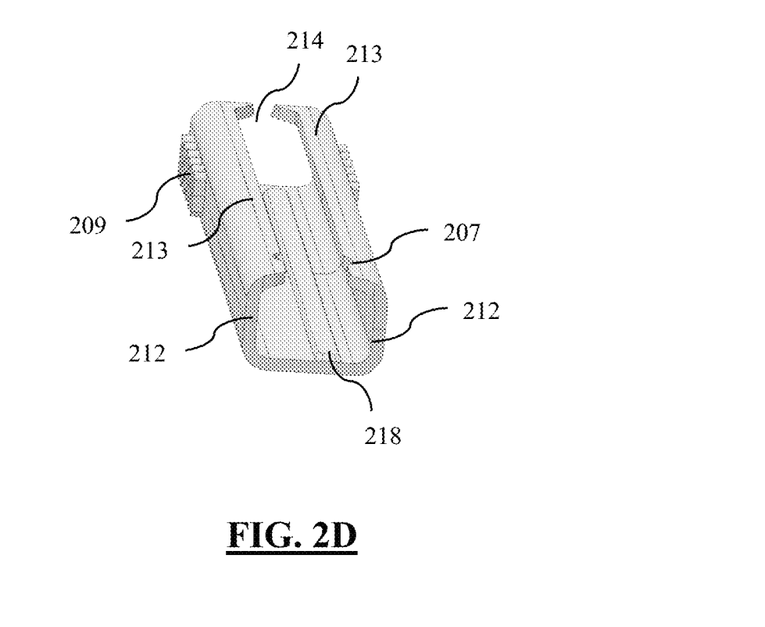
FIG. 2D illustrates a sliding portion with the retention strip, in accordance with an embodiment.

In the domain of neurostimulation, it is a well-known procedure to introduce a stylet into the leads for making positional adjustments of the leads when inserted within the anatomy of the patient. The stylet, when inserted, emerges through the lead adapter 200 via a stylet slot 216. This enables a surgeon, performing the operation, to adjust the position of the lead within the anatomy of the patient. The lead adapter 200 thus provides the unique advantage to the surgeon. Further, the lead adapter may include a retention strip 218 on the inner surface of the sliding portion 204. FIG. 2D illustrates a sliding portion 204 with the retention strip 218. The retention strip 218 may exert a required pressure on the lead contacts so that the coupling between the lead contacts and the electrical contacts of the receiving portion is robust. The thickness of the retention strip 218 may be changed according to the needs at the time of insertion of the lead. In an exemplary embodiment, the retention strip 218 may be an adhesive strip which can be coupled onto a surface of the sliding portion 204. Further, the retention strip 218 may be fabricated to have multiple thickness levels. Depending on the need, a medical professional may select a retention strip 218 of appropriate thickness during the procedure. In some further embodiments, the retention strip may be designed to run in a zig-zag manner on the inner surface of the sliding portion 204. In some instances the retention strip may be designed as, for example, a circular pattern. The retention strip 218, in some instances, may include patterns such as ribs and dots over the surface to provide additional traction to the sliding portion 204. The retention strip 218, in some embodiments, may be fabricated in a discontinuous manner in order to reduce the use of the materials. The retention strop 218 may be fabricated using at least one of, but not limited to, silicone based material, a rubber based material, an epoxy based material, and a plastic material.

Figure 2E:
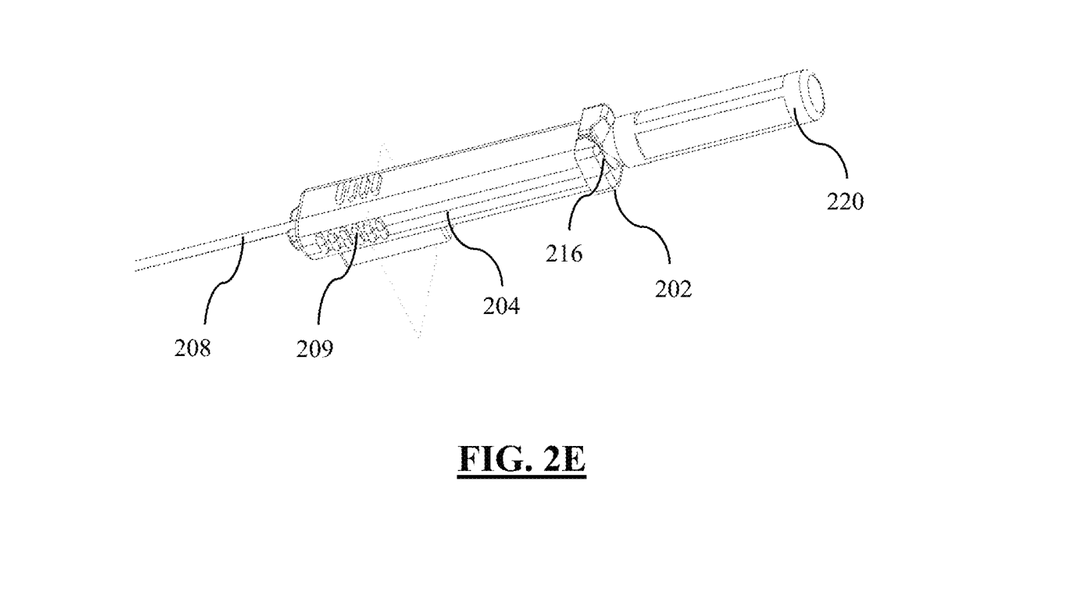
FIG. 2E illustrates the lead adapter receiving a stylet through the stylet slot, in accordance with an embodiment.

FIG. 2E illustrates the lead adapter 200 receiving a stylet 220 through the stylet slot 216. A lead 208 is inserted in the lead adapter 200. Further, the lead adapter includes a stylet slot 216. A stylet 220 may be inserted within the stylet slot 216 during the operating procedure. The stylet 220 may be used to guide the lead to the desired position within the anatomy of the subject. The surgeon may benefit from being able to modify the position of the lead 208 while the lead 208 is inserted in the lead adapter 200. The presence of the stylet slot 216 in the lead adapter 200 is a unique combination as the surgeon will have the freedom to adjust the position of the lead 208 within the patient's anatomy without needing to remove the lead 208 from the lead adapter 200. The arrangement further enables the surgeon to ensure that the lead is inserted in the right position before completing the lead insertion procedure.

In an exemplary scenario, a surgeon may be administering the trail stimulator 100 to a patient. The surgeon may have inserted the leads in the lead adapter 200 and may be in the process of attaching the lead adapter 200 to the trial stimulator unit 100. During the procedure, the surgeon may observe that the position of one of the leads has changed. The surgeon, without having to remove the lead adapter 200, may insert a stylet 200 into the stylet slot 216 and make adjustments to the position of the lead. The stylet slot 216 provides a convenient way to make adjustment to the position of the leads without having to remove the lead 208 from the lead adapter 200.

Figure 3A:
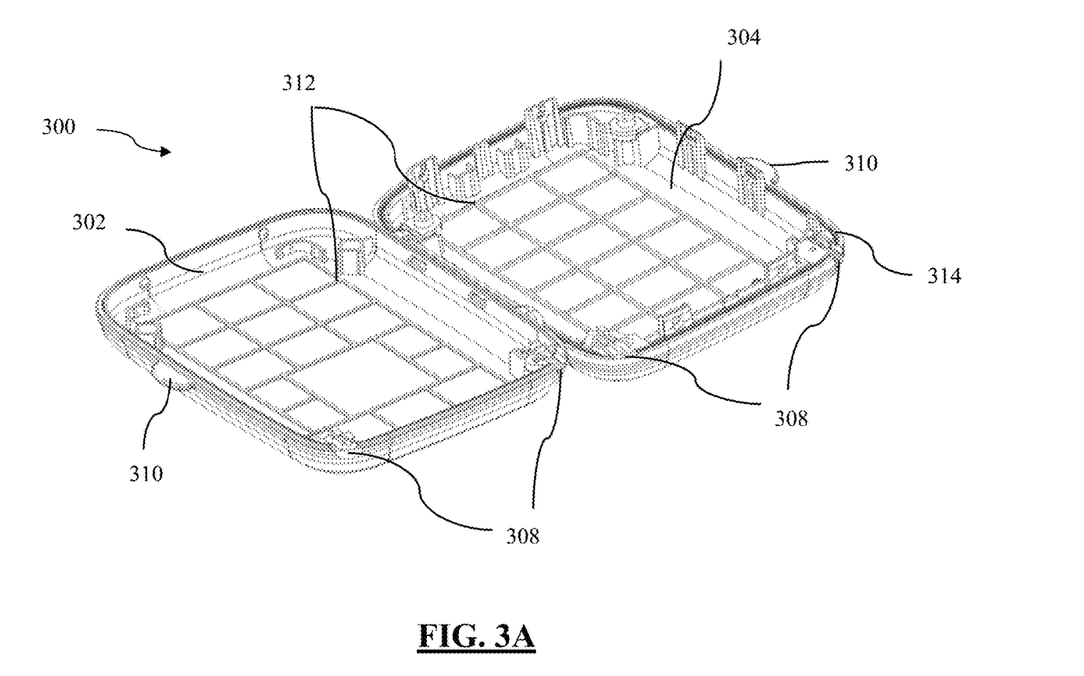
FIG. 3A illustrates a perspective view of a case for use in a trial neurostimulation system in an open state, in accordance with an embodiment.

FIG. 3A illustrates a perspective view of a case 300 for use in a trial neurostimulation system in an open state. Case 300 encloses the trial stimulator unit 100 and the lead adapters 200 along with the leads 208 inserted into the lead adapters 200. In a preferred embodiment, the case 300 includes a first portion 302 and a second portion 304 coupled by a hinged means 306. The first portion 302 and the second portion 304 may include several internally facing grooves and/or protrusions 312 corresponding to the profile of the trial stimulator unit 100 to provide stability when case 300 is in a closed state. Further, first portion 302 and second portion 304 may include grid patterns on planar surfaces to provide mechanical strength and durability. The first portion 302 and the second portion 304 further include waterproof seal or water resistant seal on the periphery to prevent any form of fluids from entering into the case 300. The first portion 302 and the second portion 304 includes a plurality of apertures 308 for allowing the leads such as lead 208, to extend from the lead adapter 200 outside case 300. The apertures 308 are configured so that a seal is formed between the perimeter of the aperture and the leads 208 passing through the apertures 308. Case 300 further includes a plurality of flaps 310 for aiding opening and closing thereof. Alternatively, the case 300 may have a locking mechanism for closing the first portion and the second portion.

The case 300 also protects the trial stimulator from environmental damage such as moisture and dust, thereby increasing the longevity of the trial stimulator unit 100. Further, case 300 allows easy replacement of the trial stimulator unit 100 in case the trial stimulator unit 100 stops working for some reason. The leader adapter 200 is easily separated from the trial stimulator and may be attached to a new trial stimulator and the stimulation may be resumed within a short period of time.

Figure 3B:
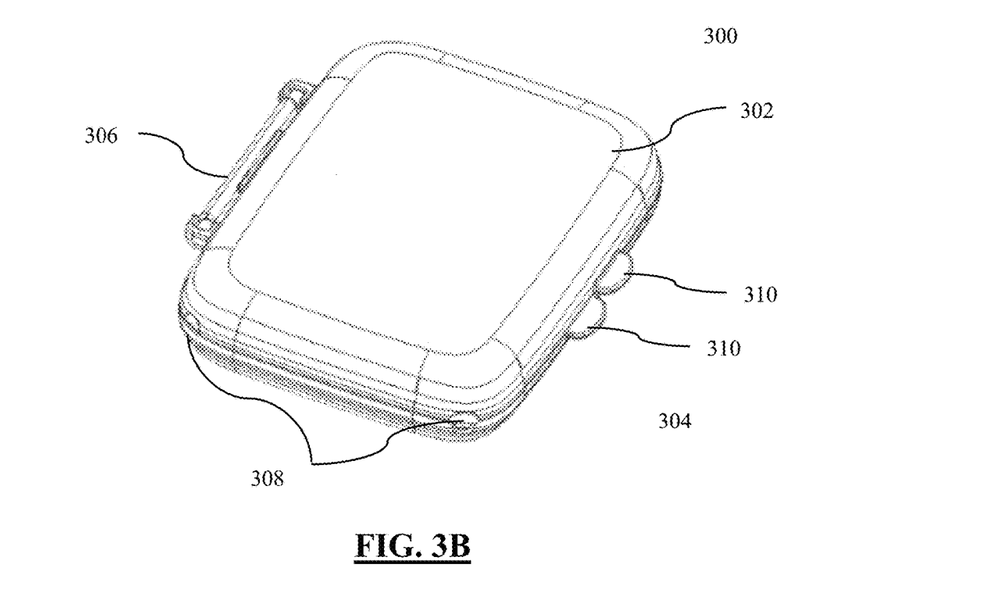
FIG. 3B illustrates a perspective view of a case for use in a trial neurostimulation system in a closed state, in accordance with an embodiment.

FIG. 3B illustrates a perspective view of the case 300 for use in a trial neurostimulation system in a closed state, in accordance with an embodiment. The case 300 in a closed state substantially encloses the trial stimulator unit 100, the lead adapters 200 and leads 208. The case 300 in a closed state protects the trial stimulator unit from any damage. Further, the case 300 is designed in a manner to maintain a robust connection between the lead adapter 200 and the trial stimulator unit 100. Further, in a closed state of case 300, the apertures 308 on the first portion 302 and second portion 304 align to form openings through which lead 208 passes through the case 300 into the lead adapter 200. In a preferred embodiment, the apertures 308 may be located at the lower periphery of the first portion 302 and the second portion 304 aligned with the receiving portion 202 of the lead adapter 200 on either side of the trial stimulator 100. It may be apparent to a person skilled in the art that the lead adapter may be coupled with the trial stimulator 100 in various orientations. As a result, the apertures 308 may be designed based on the orientation of the lead adapter 202 with the trial stimulation unit 100.

In some embodiments, the first portion 302 and the second portion 304 may be two separate parts which may be coupled together by a locking means. In another example, first portion 302 and the second portion 304 may be coupled to one another using a sliding means. In some embodiments, the outer surface of the first portion 302 may include a display unit or display window for displaying one or more parameters of the trial stimulator unit 100 such as, but not limited to, a battery level, a stimulation program and the like. In some additional embodiments, the case 300 may include one or more actuating means to control the operation of the trial stimulator unit. For example, the actuating means may include at least one of, but not limited to, a button, a knob and a keypad. In some additional embodiments, the outer surface of the first portion 302 may house a solar module. The solar module may be configured to charge the battery 112 of the trial neurostimulation system 100 when placed in sunlight.

In some other embodiments, the case 300 may be a sleeve composed of a polymer configured to enclose at least a portion of the trial stimulator unit 100 and at least one lead adapter 200. The sleeve may be composed of at least one of a material such as, but not limited to, epoxy, silicone and other polymers. The sleeve may be configured to provide waterproof or water resistant properties as it encloses the trial stimulator and the lead adapter.

Figure 4:
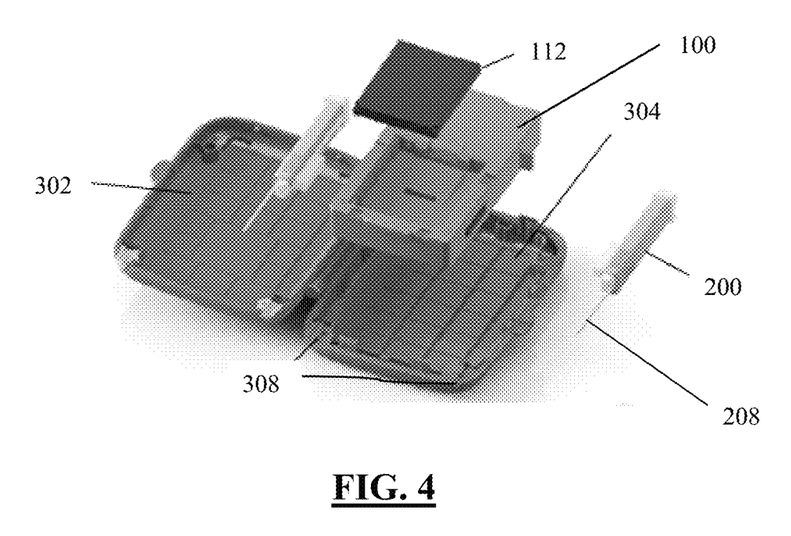
FIG. 4 illustrates an exploded view of the trial stimulator system in accordance with an embodiment.

FIG. 4 illustrates an exploded view of the trial neurostimulation system in accordance with an embodiment. FIG. 4 provides a view of the arrangement of the trial stimulator unit 100 and the lead adapters 200 with the leads 208 within the case 300. The trial stimulator unit 100 may be coupled to at least one of the first portion 302 and the second portion 304 by a friction fit mechanism. The surface of the trial stimulator 100 and the surfaces of at least one of the first portion 302 and the second portion 304 may be modified to enable the friction fit. In some embodiments, the trial stimulator unit 100 may be magnetically coupled to at least one of the first portion 302 and the second portion 304. For instance, the surface of the trial stimulator 100 may include metallic portions which in turn are configured to couple to magnets embedded in at least one of the first portion 302 and the second portion 304. The apertures 308 are configured to allow the leads 208 to pass through the case 300 and into the lead adapters 200.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A trial neurostimulation system adapted for delivering neurostimulation to a patient, the trial neurostimulation system comprising:
a trial stimulator unit for generating stimulation pulses to a targeted tissue in a patient through at least one neurostimulation lead, wherein the trial stimulator unit comprises at least one receiving connection port, wherein the receiving connection port is adapted to receive at least one lead adapter;
at least one lead adapter comprising a receiving portion, a sliding portion and a connection port, wherein the receiving portion comprises a receiving channel to receive a proximal end portion of a neurostimulation lead, wherein a plurality of electrical contacts at the receiving channel are configured to couple with corresponding electrode contacts at the proximal end portion of the neurostimulation lead, wherein the sliding portion is configured to couple to at least a part of the receiving portion by sliding the sliding portion along a movement axis that is substantially the same as an axis of the receiving channel, wherein the sliding portion comprises a retention strip configured to face the receiving channel and exert pressure on the proximal end portion of the neurostimulation lead to assist retention of the coupling between the corresponding electrode contacts at the proximal end portion of the neurostimulation lead and the plurality of electrical contacts at the receiving channel, wherein the connection port is adapted to electrically connect the electrical contacts with at least one receiving connection port; and
a case adapted to releasably contain at least a portion of the trial stimulator unit and the at least one lead adapter.

2. The trial neurostimulation system of claim 1 wherein the receiving portion comprises a stylet slot to receive a stylet, wherein the stylet is used to guide the lead to a desired location in the anatomy of a patient.

3. The trial neurostimulation system of claim 1 wherein the receiving portion comprises at least one locking portion and the sliding portion comprises at least one locking groove, wherein the locking groove is adapted to engage with the locking portion to lock the sliding portion to the receiving portion.

4. The trial neurostimulation system of claim 1 wherein the trial stimulator unit has a substantially cuboid profile.

5. The trial neurostimulation system of claim 1 wherein the trial stimulator unit comprises a battery coupled to at least one of a first surface and a second surface of the trial stimulator unit.

6. The trial neurostimulation system of claim 1 wherein the sliding portion of the plurality of lead adapter comprises one or more protrusions for better grip.

7. The trial neurostimulation system claim 1 wherein the case comprises a means to hold the trial stimulation unit in a friction fit.

8. The trial neurostimulation system of claim 1 wherein the case comprises a first portion and a second portion.

9. The trial neurostimulation system of claim 8 wherein at least one of the first portion and the second portion of the case comprises at least one of a waterproof and a water-resistant seal.

10. The trial neurostimulation system of either claim 8 wherein each of the first portion and the second portion of the case form at least one aperture, configured to accommodate the neurostimulation lead, when the case is in a closed state.

11. The trial neurostimulation system of claim 1 wherein the case further includes one or more flaps for aiding opening and closing of the case.

12. The trial neurostimulation system of claim 1 wherein the case further includes a locking mechanism for securely closing the case.

13. The trial neurostimulation system of claim 1 wherein the trial stimulator unit, the plurality of lead adapters and the case are fabricated from a group comprising plastic, epoxy, polyurethane materials.

14. The trial neurostimulation system of claim 1 wherein a battery of the trial stimulator unit is at least one of a Lithium-Ion battery, a Lithium Polymer battery and an alkaline battery.

15. A lead adapter for use with a trial neurostimulation system, the lead adapter comprising:
a receiving portion including a receiving channel to receive a proximal end of a neurostimulation lead, wherein a plurality of electrical contacts at the receiving channel are configured to couple with corresponding electrode contacts at the proximal end portion of the neurostimulation lead; and
a sliding portion, wherein the sliding portion is configured to slidingly couple with at least a part of the receiving portion by sliding the sliding portion along a movement axis that is substantially the same as an axis of the receiving channel, wherein the sliding portion comprises a retention strip configured to face the receiving channel and exert pressure on the proximal end portion of the neurostimulation lead to assist retention of the coupling between the corresponding electrode contacts at proximal end portion of the neurostimulation lead and the plurality of electrical contacts at the receiving channel.

16. The lead adapter of claim 15 wherein the receiving portion comprises at least one locking portion and the sliding portion comprises at least one locking groove, wherein the locking groove is adapted to couple with the locking portion enabling the sliding portion to slidingly couple with the receiving portion.

17. The lead adapter of claim 15 wherein the sliding portion includes lateral walls, with inwardly extending retention lips, that are slidingly receivable over at least part of the receiving portion.

18. The lead adapter of claim 15 wherein the retention strip is removable.

19. The lead adapter of claim 15 wherein a thickness of the retention strip is between a range of 0.5 mm to 1 mm.

20. The lead adapter of claim 15 wherein the sliding portion comprises a plurality of protrusions to provide grip to the sliding portion.

21. A case for enclosing a trial stimulation unit and at least one lead adapter, wherein the case comprises:
a first portion; and
a second portion,
wherein the first portion is coupled with the second portion via hinged means; and
wherein the first portion and the second portion is adapted to enclose at least a portion of the trial stimulator unit and at least one lead adapter according to claim 18.

22. The case of claim 21 wherein at least one aperture is formed when the case is in a closed state.

23. The case according to claim 22 wherein the at least one aperture is adapted to accommodate at least one neurostimulation lead.

24. The case according to claim 21 wherein at least one of the first portion and the second portion comprises at least one of a waterproof seal and a water resistant seal which renders the case waterproof and water resistant in a closed state.

* * * * *